United States Patent
Meldrum

(12) 
(10) Patent No.: US 6,447,515 B1
(45) Date of Patent: Sep. 10, 2002

(54) BIORESORBABLE IMPLANT FOR FRACTURE FIXATION

(76) Inventor: Russell Meldrum, 9925 S. Dominion Dr., Mobile, AL (US) 36695

( * ) Notice: Subject to any disclaimer, the term of this patent is extended or adjusted under 35 U.S.C. 154(b) by 229 days.

(21) Appl. No.: 09/598,509

(22) Filed: Jun. 21, 2000

(51) Int. Cl.[7] ................................. A61B 17/72

(52) U.S. Cl. .............. 606/63; 606/72; 606/77

(58) Field of Search .............. 606/60, 62, 63, 606/64, 67, 68, 72, 73, 77, 95, 105; 623/16.11, 17.12, 17.13

(56) References Cited

U.S. PATENT DOCUMENTS

| | | | |
|---|---|---|---|
| 4,313,434 A | * | 2/1982 | Segal |
| 5,102,413 A | * | 4/1992 | Poddar |
| 5,531,792 A | * | 7/1996 | Huene |

* cited by examiner

*Primary Examiner*—David O. Reip
(74) *Attorney, Agent, or Firm*—H. Jay Spiegel

(57) ABSTRACT

The present invention contemplates use of a resorbable ceramic or other material inserted into a special container, the outer dimensions of which may be adjusted during insertion to provide firm fixation of a fracture. The special container consists of two spaced plugs connected together with a flexible boot and including actuator means allowing adjustment of the spacing between the plugs. The volume enclosed within the plugs and boot is filled with the resorbable ceramic material. As the actuator means moves the plugs toward one another, the material is squeezed and tends to expand radially outwardly, stretching the boot and increasing the outer diameter of the special container to wedge and fixate the container in the desired position within the location of the fracture. In the preferred embodiments of the present invention, all of the components of the special container are bioresorbable. Alternative materials to the resorbable ceramic material can include Collagen Sponge and Demineralized Bone Matrix or Proteins.

22 Claims, 2 Drawing Sheets

BIORESORBABLE IMPLANT FOR FRACTURE FIXATION

BACKGROUND OF THE INVENTION

Surgeons fix millions of fractures annually using traditional metal alloy or stainless steel implants that become useless and occasionally painful after the fracture has been united. In many cases, in order to prevent the complications and risks associated with the placement and removal of these metal implants, bioresorbable screws and other similar devices have been developed. Such resorbable implants allow for fixation while a slow controlled resorption is underway.

However, where a fracture consists of a metaphyseal or diaphyseal fracture of a long bone such as, for example, the femur, the need has developed for a fracture fixating implant that is significantly larger in dimensions than the typical fixation screw but which is also resorbable to avoid the necessity of secondary surgery to remove fixating components. It is with this thought in mind that the present invention was developed.

SUMMARY OF THE INVENTION

The present invention relates to a bioresorbable implant for fracture fixation. The present invention includes the following interrelated objects, aspects and features:

(1) The present invention contemplates the use of a resorbable ceramic material inserted into a special container, the outer dimensions of which may be adjusted during insertion to provide firm fixation. In the preferred embodiment, the ceramic material consists of a material such as Calcium Sulfate (otherwise known as Plaster of Paris) or Hydroxyapatite. Such materials have the characteristic of being mixable in a paste-like form and which begin to set up and harden within several minutes to an hour of their first mixing. Alternative materials that could be employed with equal effectiveness include Collagen Sponge which acts as a scaffolding for the incorporation of bone as proteins are deposited on it, cells invade and it is turned into bone; and Demineralized Bone Matrix or Proteins: the proteins act as a scaffolding in a similar manner as is the case with the Collagen Sponge but it is not organized and it is extracted from existing bone; the protein promotes rapid incorporation and is able to turn the tissue adjacent to the proteins into bone through a process called Osteoinduction.

(2) The special container in which the resorbable ceramic or other material is placed preferably consists of two spaced plugs or plates connected together with a flexible boot and including actuator means allowing adjustment of the spacing between the plugs or plates.

(3) The volume enclosed within the plugs and boot is filled with the resorbable ceramic or other material. As should be understood, as the mechanism moves the plugs toward one another, the material is squeezed and tends to expand radially outwardly, stretching the boot and increasing the outer diameter of the special container. Through this process, the special container can be wedged and fixated in desired position within the location of the fracture.

(4) In the preferred embodiment of the present invention, all of the components of the special container are also bioresorbable so that as the fracture heals, the special container along with the material therein are resorbed within the body as the bone regenerates at the fracture site so that secondary surgery is not required.

(5) In a first embodiment of the special container, the actuator means consists of a spring biasing the two plugs together and a plunger that may be manipulated by the surgeon to separate the plugs to make the outer dimensions of the special container as thin as possible when it is being placed at the fracture site. When pressure is released on the plunger, the spring biasing force moves the plugs toward one another to expand the material outwardly against the flexible boot to wedge and fixate the special container in place.

(6) In a second embodiment of the present invention, a central shaft or rod is threaded through both of the plates. One plate has right-hand threads in an opening therethrough and the other plate has left-hand threads in an opening therethrough. The rod has threads complementary to each of the right-hand and left-hand threads in the respective plates, such that rotation of the rod in one direction causes the plates to move toward one another and rotation of the rod in the opposite direction causes the plates to move away from one another. Thus, with the material inserted within the special container, the rod is rotated to separate the plates from one another as far as possible so that the special container adopts the thinnest possible profile. After the special container is inserted within the fracture site, the rod is rotated in the opposite direction to move the plates toward one another and cause the material to spread outwardly expanding the flexible boot and wedging the special container at the fracture site.

Accordingly, it is a first object of the present invention to provide a bioresorbable implant for fracture fixation.

It is a further object of the present invention to provide such a device in which a resorbable ceramic material is contained within a resorbable special container having an actuator means allowing it to be placed at a fracture site and wedged in place to provide fracture fixation.

It is a further object of the present invention to provide such a device in which a Collagen Sponge material is contained within the resorbable special container.

It is a still further object of the present invention to provide such a device in which Demineralized Bone Matrix or Proteins are contained within the special container.

It is a still further object of the present invention to provide such a device in which two spaced plugs are connected by a flexible boot to define an internal chamber containing the resorbable ceramic material.

It is a yet further object of the present invention to provide an embodiment in which a spring provides a biasing force tending to move the plates toward one another.

It is a yet further object of the present invention to provide such a device in which right-hand and left-hand threads are used in an actuator mechanism designed to move the plates toward and away from one another.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
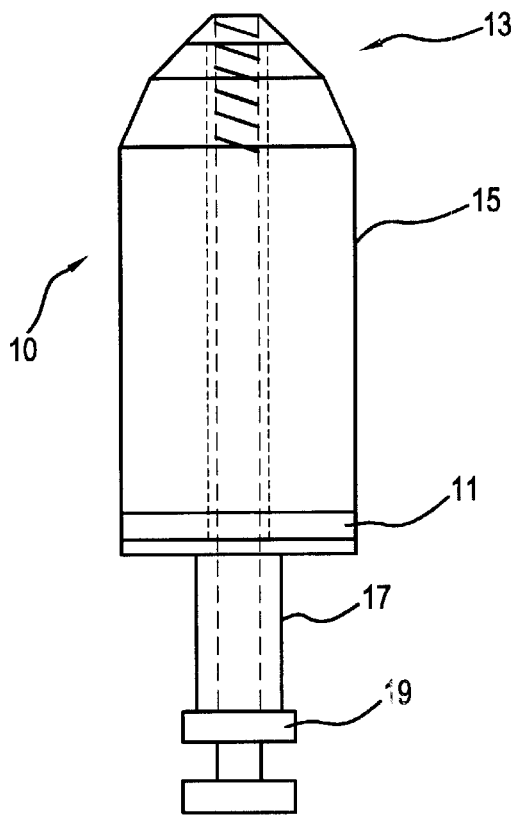
FIG. 1 shows a side view of a first embodiment of the present invention.
Figure 2:
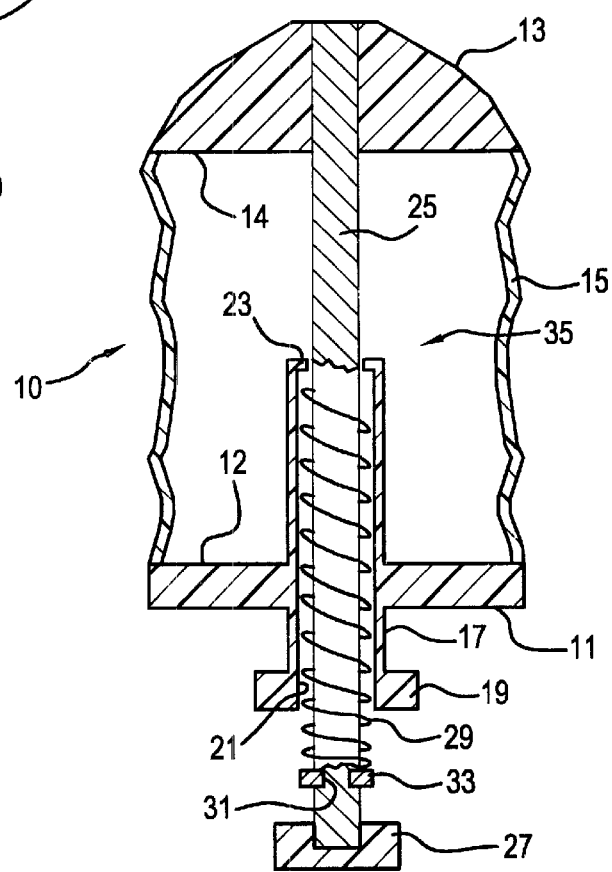
FIG. 2 shows a view partially in cross-section of the embodiment of FIG. 1.
Figure 3:
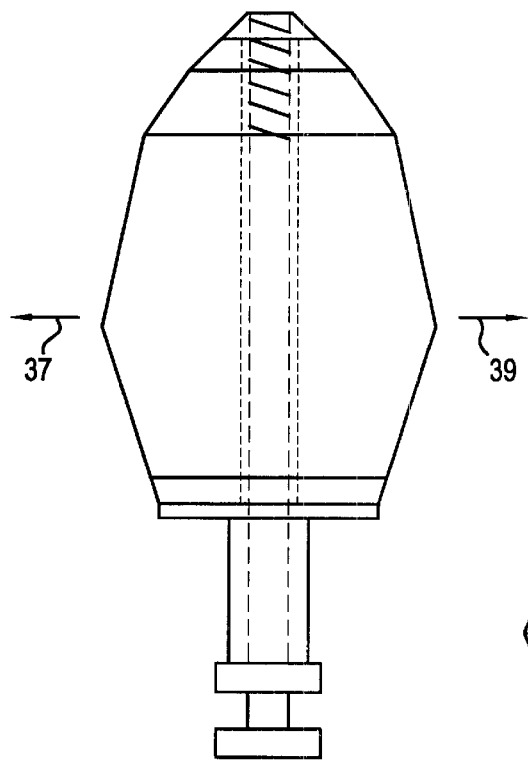
FIG. 3 shows a further side view of the embodiment of FIGS. 1 and 2 showing the expansion of the flexible boot in the radially outward direction.

With reference, first, to FIGS. 1–3, a first embodiment of the present invention is generally designated by the reference numeral 10 and is seen to include a first plug 11, a second plug 13 and a flexible boot 15. The plug 11 is generally cylindrical and the plug 13 preferably includes three frustoconical sections integrally formed together. The plug 13 comprises the distal end of the inventive implant and is intended to be inserted into a metaphyseal or diaphyseal fracture of a long bone such as, for example, a femur.

With further reference to FIGS. 1 and 2, the plug 11 includes an integrally formed shoulder 17 having a proximal hub 19. The shoulder and hub define an internal passageway 21 (FIG. 2) that terminates distally in a shoulder 23, for a purpose to be described in greater detail hereinafter. The plug 13 has an elongated shaft 25 attached thereto which extends through the passageway 21 and terminates at a removable gripping knob or cap 27. As seen in FIG. 2, a compression spring 29 is received within the passageway 21 and engages the shoulder 23 at one end and a snap ring 33 received within a recess 31 in the shaft 25 at the other end. As should be understood from FIG. 2, the force exerted by the spring 29 tends to move the plugs 11 and 13 toward one another.

The plug 11 has an inner surface 12 and the plug 13 has an inner surface 14. The surfaces 12 and 14 together with the flexible boot 15 define an internal chamber 35. In the preferred embodiment of the present invention, when the inventive implant 10 is used during performance of fracture fixation surgery, the chamber 35 is filled with a resorbable ceramic material that may initially be mixed in a malleable paste which fixates and begins to harden within a few minutes to an hour after mixing. Examples of resorbable ceramic materials that may be employed for this purpose include Calcium Sulfate (otherwise known as Plaster of Paris) and Hydroxyapatite.

As should be understood from FIGS. 1–3, the plate or plug 13 has an outer configuration designed so that its outer walls impale and compress an inner bone when the inventive device is shortened (the plugs 11 and 13 drawn closer together) as will be explained in greater detail hereinafter.

In use of the inventive implant 10, resorbable ceramic material is inserted within the chamber 35 in any desired manner. For example, the flexible boot 15 may be designed to be removable from one of the plugs 11, 13 to provide an opening to allow insertion of the resorbable ceramic material. Any suitable means for accomplishing this end may suitably be employed.

Thereafter, the shaft 25 is reciprocated by depressing the gripping knob or cap 27 toward the proximal hub 19 against the spring force of the spring 29. Such action separates the surfaces 14 and 12 of the plugs 13 and 11, respectively, and causes the implant 10 to assume its thinnest configuration. Any desired surgical technique can then be employed to place the inventive implant in its desired location. For example, insertion can be accomplished at either end of the bone where access to the intramedullary canal thereof can be achieved. A sound and/or guide-wire can be advanced across the fracture to create a path for the implant while the fracture is held in position by known means. As an alternative, sequential sounds or reamers of increasing diameters may be passed across the fracture to measure the inner diameter of the bone's canal and provide a clear and unobstructed path for placement of the implant. Through use of fluoroscopy and, perhaps, over a guide-wire, the implant is sent down the intramedullary canal. The plug or plate 13 with its frustoconical outer shape is sent across the fracture and, as can clearly be seen in FIG. 2, has a diameter that increases in the direction of the plug 11. With the implant in place, pressure on the shaft 25 tending to move the gripping knob or cap 27 toward the proximal hub 19 is released causing the compression spring 29 to move in a direction causing the surfaces 14 and 12 of the plates or plugs 13 and 11, respectively, to move toward one another (FIG. 3), thereby causing the flexible boot 15 to expand outwardly in the direction of the arrows 37 and 39. As a result, the overall outer diameter of the implant 10 increases causing it to be wedged into position within the fracture site.

In the preferred embodiment, not only is the ceramic material resorbable but the entire implant 10 is made of resorbable materials such as, for example, Poly-lactic Acid. Thus, as the fracture is fixating and healing, all of the components of the implant 10 and the resorbable ceramic material contained within the chamber 35 gradually resorb into the patient's body until, eventually, there is no sign of the prior presence of the implant 10. In this way, secondary surgery to remove the implant is eliminated.

While use of a resorbable ceramic material comprises the preferred embodiment of the present invention, other materials may also be employed with equally effective results. One alternative material consists of Collagen Sponge. Such a sponge acts as a scaffolding for the incorporation of bone as proteins are deposited upon it and cells invade, thereby turning it into bone. Such a material is typically manufactured in a laboratory.

A second alternative material consists of Demineralized Bone Matrix or Proteins. Such proteins act as a scaffolding in a similar manner as is the case with Collagen Sponge but they are not organized in the same manner and are extracted from existing bone. The proteins promote rapid incorporation and are able to turn the tissue adjacent to the proteins into bone through a process known as Osteoinduction.

Figure 4:
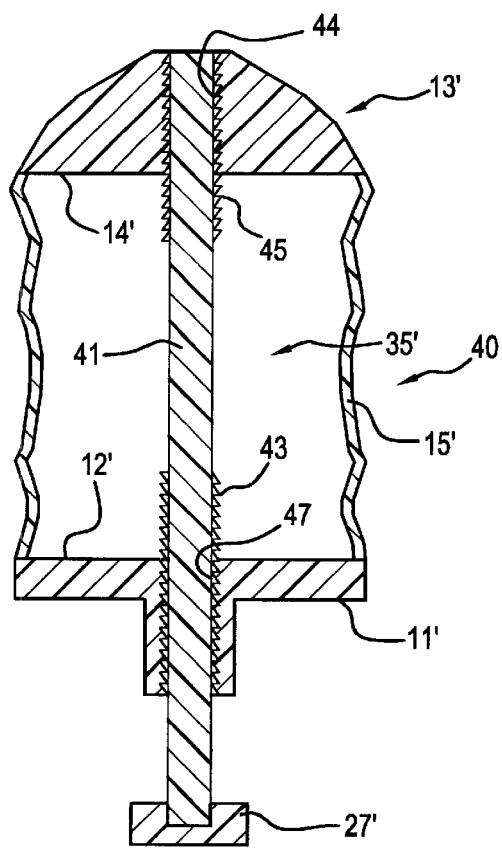
FIG. 4 shows a side cross-sectional view of a second embodiment of the present invention.

Reference is now made to FIG. 4 so that a description of a second embodiment 40 may be made. In FIG. 4, like elements from the embodiment of FIGS. 1–3 are described using like primed reference numerals. The principle of operation of the implant 40 is the same as that of the implant 10. The difference lies in the specific mechanism for actuating the implant 40 to move the plates or plugs 11', 13' toward and away from one another. Thus, the implant 40 includes an elongated shaft 41 that has left-hand threads 43 at the proximal end thereof and right-hand threads 45 at the distal end thereof. The plate or plug 11' has an internal passageway 47 having left-hand threads complementary to the left-hand threads 43 while the plate or plug 13' includes an internal passageway 49 having right-hand threads complementary to the right-hand threads 45. Thus, the movement of the plates or plugs 11', 13' is accomplished in a similar manner to the operation of a turnbuckle. As should be understood, rotation of the shaft 41 in one direction moves the surfaces 12' and 14' toward one another, whereas rotation of the shaft 41 in the opposite direction moves the surfaces 12' and 14' away from one another. Thus, the surgeon may rotate the shaft 41 in the desired direction to separate the surfaces 12' and 14' as far as possible to give the device 40 its thinnest possible outer dimensions. Of course, the locations of the right-hand and left-hand threads may be reversed. With a resorbable ceramic or other material inserted within the chamber 35' in any desired manner, the implant 40 is placed in position by any desired surgical technique such as those described hereinabove with regard to the embodiment of FIGS. 1–3 and, thereafter, the shaft 41 is rotated in the opposite direction to move the surfaces 12' and 14' toward one another to cause the material within the chamber 35' to expand out the boot 15' in the same manner as is depicted in FIG. 3 concerning the embodiments of FIGS. 1–3 to cause the implant 40 to be wedged and fixated in place at the site of a metaphyseal or diaphyseal fracture of a long bone such as a femur.

As is the case with the embodiment of FIG. 1, the implant 40 is preferably made entirely of a bioresorbable material such as, for example, Poly-lactic Acid. Of course, any other resorbable material that has sufficient structural integrity to allow it to be formed into an implant such as the implant 10 or 40 but which allows bioresorbability may suitably be employed.

As such, an invention has been disclosed in terms of preferred embodiments thereof which fulfill each and every one of the objects of the invention as set forth hereinabove and provide a new and useful bioresorbable implant for fracture fixation of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. A bioresorbable implant for fracture fixation, comprising:
   a) a first plug and a second plug;
   b) a flexible boot interconnected between said plugs to define an internal chamber;
   c) actuator means for moving said plugs toward and away from one another; and
   d) a material within said chamber, said material placed within said chamber in a malleable state.

2. The implant of claim 1, wherein said first plug is generally cylindrical.

3. The implant of claim 1, wherein said second plug is generally frustoconical.

4. The implant of claim 3, wherein said first plug is generally cylindrical.

5. The implant of claim 1, made of a resorbable material.

6. The implant of claim 5, wherein said resorbable material comprises Poly-lactic Acid.

7. The implant of claim 1, wherein said material comprises a resorbable ceramic material.

8. The implant of claim 7, wherein said resorbable ceramic material is chosen from the group consisting of Calcium Sulfate and Hydroxyapatite.

9. The implant of claim 1, wherein said material comprises Collagen Sponge.

10. The implant of claim 1, wherein said material comprises Demineralized Bone Matrix or Proteins.

11. The implant of claim 1, wherein said actuator means comprises spring biasing means for biasing said plugs toward one another and an elongated rod operable to move said plugs away from one another.

12. The implant of claim 11, wherein said rod is attached to said second plug.

13. The implant of claim 12, wherein said rod extends through an opening in said first plug.

14. The implant of claim 13, wherein said rod has a gripping knob at an end thereof remote from said second plug.

15. The implant of claim 13, wherein said material comprises a resorbable ceramic material chosen from the group consisting of Calcium Sulfate and Hydroxyapatite.

16. The implant of claim 1, wherein said actuator means comprises an elongated rod having a proximal end and a distal end, said rod having one of right-hand or left-hand threads at its proximal end and the other of right-hand or left-hand threads at its distal end, said first plug having an opening with threads complementary to said proximal end threads and said second plug having an opening with threads complementary to said distal end threads, whereby rotation of said rod in a first direction causes said plugs to move toward one another and rotation of said rod in a second opposite direction causes said plugs to move away from one another.

17. The implant of claim 16, wherein said second plug is generally frustoconical.

18. The implant of claim 17, wherein said first plug is generally cylindrical.

19. The implant of claim 16, made of a resorbable material comprising Poly-lactic Acid.

20. The implant of claim 16, wherein said material comprises a resorbable ceramic material.

21. A bioresorbable implant for fracture fixation, comprising:
   a) a first cylindrical plug and a second generally frustoconical plug;
   b) a flexible boot interconnected between said plugs to define an internal chamber;
   c) actuator means for moving said plugs toward and away from one another, said actuator means comprising an elongated rod having a proximal end and a distal end, said rod having one of right-hand or left-hand threads at its proximal end and the other of right-hand or left-hand threads at its distal end, said first plug having an opening with threads complementary to said proximal end threads and said second plug having an opening with threads complementary to said distal end threads, whereby rotation of said rod in a first direction causes said plugs to move toward one another and rotation of said rod in a second opposite direction causes said plugs to move away from one another;
   d) a material within said chamber, said material placed within said chamber in a malleable state, said material being chosen from the group consisting of bioresorbable ceramic, Collagen Sponge and Demineralized Bone Matrix or Proteins; and
   e) said implant made from a resorbable material.

22. The implant of claim 21, wherein said resorbable material comprises Poly-lactic Acid.

* * * * *